US00PP15869P2

(12) United States Plant Patent
Dümmen

(10) Patent No.: US PP15,869 P2
(45) Date of Patent: Jul. 19, 2005

(54) ***OSTEOSPERMUM* PLANT NAMED 'DUESUMPUR'**

(50) Latin Name: *Osteospermum ecklonis*
Varietal Denomination: Duesumpur

(75) Inventor: Marga Dümmen, Rheinberg (DE)

(73) Assignee: Dümmen Jungpflanzen, Rheinberg (DE)

( * ) Notice: Subject to any disclaimer, the term of this patent is extended or adjusted under 35 U.S.C. 154(b) by 34 days.

(21) Appl. No.: 10/859,518

(22) Filed: Jun. 1, 2004

(51) Int. Cl.[7] ..... A01H 5/00
(52) U.S. Cl. ..... Plt./360
(58) Field of Search ..... Plt./360

(56) References Cited

PUBLICATIONS

UPOV–ROM GTITM Computer Database 2004/04, GTI Jouve Retrieval Software, Citation for 'Duesumpur'.*

* cited by examiner

*Primary Examiner*—Anne Marie Grunberg
*Assistant Examiner*—Annette H Para
(74) *Attorney, Agent, or Firm*—C. A. Whealy

(57) ABSTRACT

A new and distinct cultivar of *Osteospermum* plant named 'Duesumpur', characterized by its compact and uniformly mounded plant habit; Freely branching growth habit; freely and early flowering habit; and inflorescences with purple-colored ray florets.

1 Drawing Sheet

Botanical classification/cultivar designation: *Osteospermum ecklonis* cultivar Duesumpur.

BACKGROUND OF THE INVENTION

The present Invention relates to a new and distinct cultivar of *Osteospermum* plant, botanically known as *Osteospermum ecklonis,* and hereinafter referred to by the name 'Duesumpur'.

The new *Osteospermum* is a product of a planned breeding program conducted by the Inventor in Rheinberg, Germany. The objective of the breeding program is to create new compact *Osteospermum* cultivars with uniform plant habit, early flowering and interesting floret coloration.

The new *Osteospermum* originated from a cross-pollination made by the Inventor in July, 2000 of a proprietary selection of *Osteospermum ecklonis* identified as code number F-19-05, not patented, as the female, or seed, parent with a proprietary selection of *Osteospermum ecklonis* identified as code number F-13-01, not patented, as the male, or pollen, parent. The new *Osteospermum* was discovered and selected by the Inventor as a single flowering plant within the progeny of the stated cross-pollination grown in a controlled environment in Rheinberg, Germany in May, 2002.

Asexual reproduction of the new *Osteospermum* by vegetative tip cuttings was first conducted in Rheinberg, Germany in June, 2002. Asexual reproduction by cuttings has shown that the unique features of this new *Osteospermum* are stable and reproduced true to type in successive generations.

SUMMARY OF THE INVENTION

The cultivar Duesumpur has not been observed under all possible environmental conditions. The phenotype may vary somewhat with variations in environment such as temperature and light intensity without, however, any variance in genotype.

The following traits have been repeatedly observed and are determined to be the unique characteristics of 'Duesumpur'. These characteristics in combination distinguish 'Duesumpur' as a new and distinct *Osteospermum.*

1. Compact and uniformly mounded plant habit.
2. Freely branching growth habit; full and dense plants.
3. Freely and early flowering habit.
4. Inflorescences with purple-colored ray florets.

In side-by-side comparisons conducted in Rheinberg, Germany, plants of the new *Osteospermum* differed from plants of the female parent selection in the following characteristics:

1. Plants of the new *Osteospermum* were more compact than plants of the female parent selection.
2. Plants of the new *Osteospermum* and the female parent selection differed in ray floret coloration.

In side-by-side comparisons conducted in Rheinberg, Germany, plants of the new *Osteospermum* differed from plants of the male parent selection in the following characteristics:

1. Plants of the new *Osteospermum* had larger inflorescences than plants of the male parent selection.
2. Plants of the new *Osteospermum* and the male parent selection differed in ray floret coloration.

Plants of the new *Osteospermum* can be compared to plants of the cultivar Westside, not patented. In side-by-side comparisons conducted in Rheinberg, Germany, plants of the new *Osteospermum* differed from plants of the cultivar Westside, in the following characteristics:

1. Plants of the new *Osteospermum* were more compact than plants of the cultivar Westside.
2. Plants of the new *Osteospermum* flowered about one week earlier than plants of the cultivar Westside.

BRIEF DESCRIPTION OF THE PHOTOGRAPH

The accompanying colored photograph illustrates the overall appearance of the new *Osteospermum* showing the colors as true as it is reasonably possible to obtain in colored reproductions of this type. Colors in the photograph may differ from the color values cited in the detailed botanical description which accurately describe the colors of the new *Osteospermum*.

The photograph comprises a side perspective view of a typical flowering plant of 'Duesumpur' grown in container.

DETAILED BOTANICAL DESCRIPTION

In the following description, color references are made to The Royal Horticultural Society Colour Chart, 1995 Edition, except where general terms of ordinary dictionary significance are used.

The aforementioned photographs, following observations and measurements describe plants grown during the spring in Rheinberg, Germany, in a glass-covered greenhouse and under conditions which approximate those generally used in commercial *Osteospermum* production. Single plants were grown in 13-cm containers and pinched once about one week after planting. During the production of the plants, day and night temperatures were about 18° C. and light levels were about 4,500 foot-candles. Measurements and numerical values represent averages of typical flowering plants about 16 weeks after planting.

Botanical classification: *Osteospermum ecklonis* cultivar Duesumpur.

Parentage:

*Female, or seed, parent.*—Proprietary selection of *Osteospermum ecklonis* identified as code number F-19-05, not patented.

*Male, or pollen, parent.*—Proprietary selection of *Osteospermum ecklonis* identified as code number F-13-01, not patented.

Propagation:

*Type.*—Terminal cuttings.

*Time to initiate roots.*—About 10 days at 20° C.

*Time to develop roots.*—About three weeks at 20° C.

*Root description.*—Fibrous, fine; white in color.

*Rooting habit.*—Freely branching.

Plant description:

*Appearance.*—Perennial herbaceous container and garden plant. Compact and uniformly mounded plant habit; upright and somewhat outwardly spreading; inverted triangle. Freely branching, about six primary lateral branches; dense and full plants. Moderately vigorous growth habit.

*Plant height.*—About 15 cm.

*Plant width or area of spread.*—About 14 cm.

*Lateral branches.*—Length: About 14 cm. Diameter: About 5 mm. Internode length: About 7.6 mm. Strength: Strong. Texture: Glabrous, smooth. Color: 144B.

*Foliage description.*—Arrangement: Alternate; simple. Length: About 4 cm. Width: About 2.5 cm. Shape: Spatulate. Apex: Acute. Base: Attenuate. Margin: Dentate; sinuses divergent. Venation pattern: Pinnate. Texture, upper surface: Leathery; pubescent. Texture, lower surface: Leathery; glabrous. Color: Developing foliage, upper surface: 137B. Developing foliage, lower surface: 144A. Fully expanded foliage, upper surface: 137A. Fully expanded foliage, lower surface: 137B. Venation, upper and lower surfaces: 144B. Petiole: Length: About 7.8 cm. Diameter: About 4.8 mm. Texture, upper and lower surfaces: Glabrous. Color, upper surface: 144B to 144C. Color, lower surface: 144A.

Inflorescence description:

*Appearance.*—Terminal and axillary inflorescences held above and beyond the foliage. Composite inflorescence form, radially symmetrical, with ligulate-shaped ray florets and disc florets massed at the center; ray and disc florets arranged acropetally on a capitulum. Inflorescences face upright or outwardly.

*Flowering response.*—Plants flower continuous and freely from the spring through the fall. Early flowering, plants begin to flower about six weeks after planting.

*Postproduction longevity.*—Inflorescences maintain good color and substance for about three days on the plant. Inflorescences not persistent.

*Quantity of inflorescences.*—Freely flowering; about 45 open inflorescences and inflorescence buds per plant.

*Fragrance.*—None detected.

*Inflorescence bud.*—Length: About 1.4 cm. Diameter: About 6.3 mm. Shape: Ovoid. Color: 137B and 144C to 144D.

*Inflorescence size.*—Diameter: About 4 cm. Depth (height): About 2 cm. Disc diameter: About 8.5 mm. Receptacle diameter: About 4 mm. Receptacle height: About 3 mm.

*Ray florets.*—Length: About 2.3 cm. Width: About 7.2 mm. Shape: Elongated oblong. Apex: Emarginate. Base: Obtuse. Margin: Entire. Texture, upper and lower surfaces: Smooth; velvety. Orientation: Initially 30° from vertical, with development, close to 60° from vertical. Number of ray florets per inflorescence: About 17 to 18 in a single whorl. Color: When opening, upper surface: 87D; towards the base, lighter than 87D. When opening, lower surface: 91B; longitudinal stripes, close to 87A. Fully opened, upper surface: 77B; towards the base, lighter than 77B. Fully opened, lower surface: 91B; longitudinal stripes, close to 87A.

*Disc florets.*—Shape: Tubular, elongated. Apex: Five-pointed. Length: About 5 mm. Width: At apex: About 2 mm. At base: Less than 1 mm. Number of disc florets per inflorescence: About 50. Color: Immature: More gray than 94B. Mature: Apex: 97B. Mid-section: 155A. Base: 157A.

*Phyllaries.*—Length: About 1 cm. Diameter: About 2 mm. Shape: Lanceolate. Apex: Apiculate. Base: Fused. Margin: Entire. Texture, upper and lower surfaces: Leathery. Number per inflorescence: About 15 in a single whorl. Color, upper surface: 137B to 137C. Color, lower surface: 137C.

*Peduncles.*—Length, terminal peduncle: About 7 cm. Diameter: About 2 mm. Strength: Strong. Texture: Leathery. Color: 144A.

*Reproductive organs.*—Androecium: Present on disc florets only. Stamen number: Five per floret; fused around style. Anther shape: Oblong. Anther length: About 2 mm. Anther color: 98A. Pollen amount: Abundant. Pollen color: 23A. Gynoecium: Present on both ray and disc florets. Pistil number: One per floret. Pistil length: About 7 mm. Stigma shape: Two-parted. Stigma color: 79A. Style length: About 3 mm. Style color: 79A. Ovary color: 144C.

*Seed.*—Length: About 7 mm. Diameter: About 3 mm. Color: 199A.

Disease/pest resistance: Resistance to pathogens and pests common to *Osteospermum* has not been observed on plants grown under commercial greenhouse or outdoor conditions.

Temperature tolerance: Plants of the new *Osteospermum* have been observed to tolerate temperatures from 5 to 35° C.

It is claimed:

1. A new and distinct cultivar of *Osteospermum* plant named 'Duesumpur', as illustrated and described.

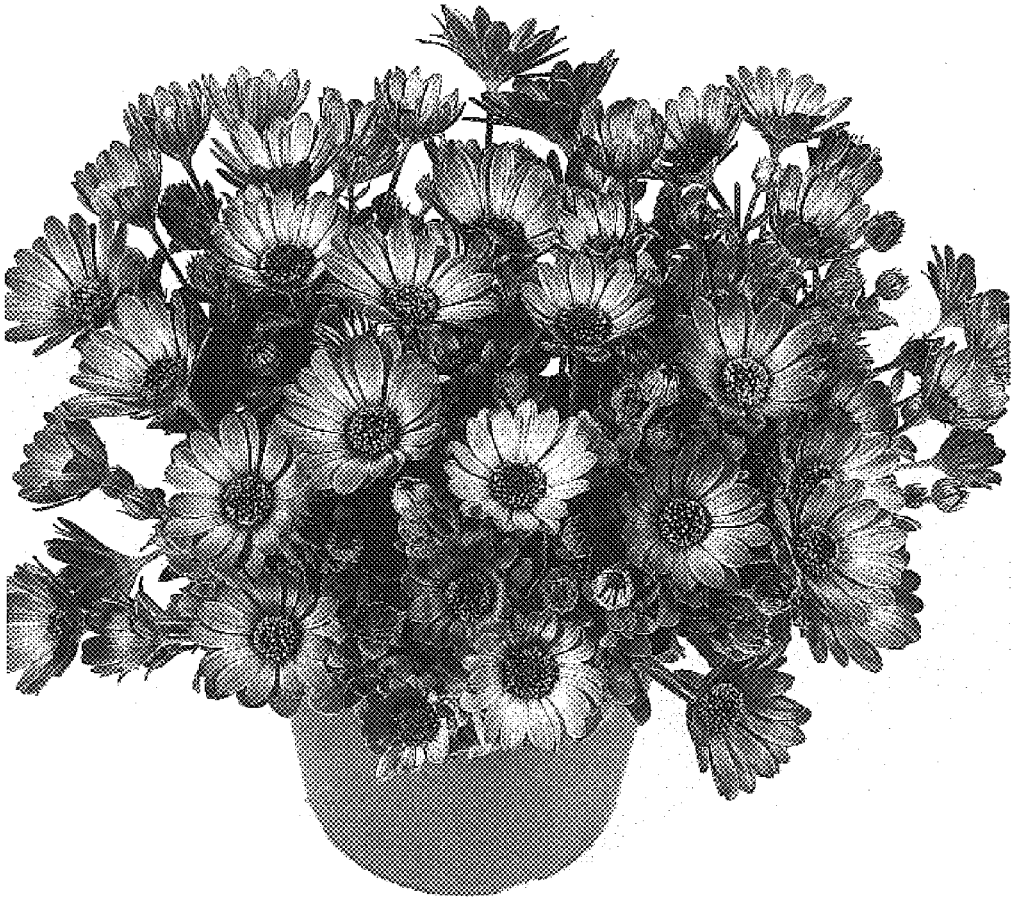

* * * * *